(12) United States Patent
Son et al.

(10) Patent No.: US 12,264,346 B2
(45) Date of Patent: Apr. 1, 2025

(54) MODIFIED POLYPEPTIDE HAVING MANNANASE ACTIVITY

(71) Applicant: CJ CHEILJEDANG CORPORATION, Seoul (KR)

(72) Inventors: Byung-sam Son, Seoul (KR); Hyun Kug Cho, Seoul (KR); Eun Jung Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 17/905,064

(22) PCT Filed: Jul. 25, 2022

(86) PCT No.: PCT/KR2022/010853
§ 371 (c)(1),
(2) Date: Aug. 25, 2022

(87) PCT Pub. No.: WO2023/146041
PCT Pub. Date: Aug. 3, 2023

(65) Prior Publication Data
US 2024/0376458 A1    Nov. 14, 2024

(30) Foreign Application Priority Data
Jan. 26, 2022   (KR) ........................ 10-2022-0011725

(51) Int. Cl.
*C12N 15/02*   (2006.01)
*A23J 3/34*    (2006.01)
*C11D 3/386*   (2006.01)
*C12N 9/24*    (2006.01)
*C12N 15/09*   (2006.01)
*C12P 19/02*   (2006.01)
*C12P 19/04*   (2006.01)
*C12P 19/14*   (2006.01)
*C12P 21/06*   (2006.01)

(52) U.S. Cl.
CPC ............ *C12N 9/2494* (2013.01); *C12P 19/02* (2013.01); *C12P 19/04* (2013.01); *C12P 19/14* (2013.01); *C12Y 302/01078* (2013.01)

(58) Field of Classification Search
CPC .......... C12N 9/24; C12N 15/02; C12N 15/09; C12P 19/14; C12P 19/04; A23J 3/34; C11D 3/386; C12Y 302/01078
See application file for complete search history.

(56) References Cited

FOREIGN PATENT DOCUMENTS

| KR | 10-2016-0045465 A | 4/2016 |
|---|---|---|
| WO | WO 2017/079756 A1 | 5/2017 |
| WO | WO 2018/206302 A1 | 11/2018 |
| WO | WO 2018/220273 A1 | 12/2018 |

*Primary Examiner* — Maryam Monshipouri
(74) *Attorney, Agent, or Firm* — Squire Patton Boggs (US) LLP

(57) ABSTRACT

Disclosed is a modified polypeptide having mannanase activity and a use thereof.

13 Claims, 2 Drawing Sheets
Specification includes a Sequence Listing.

[Fig. 1]
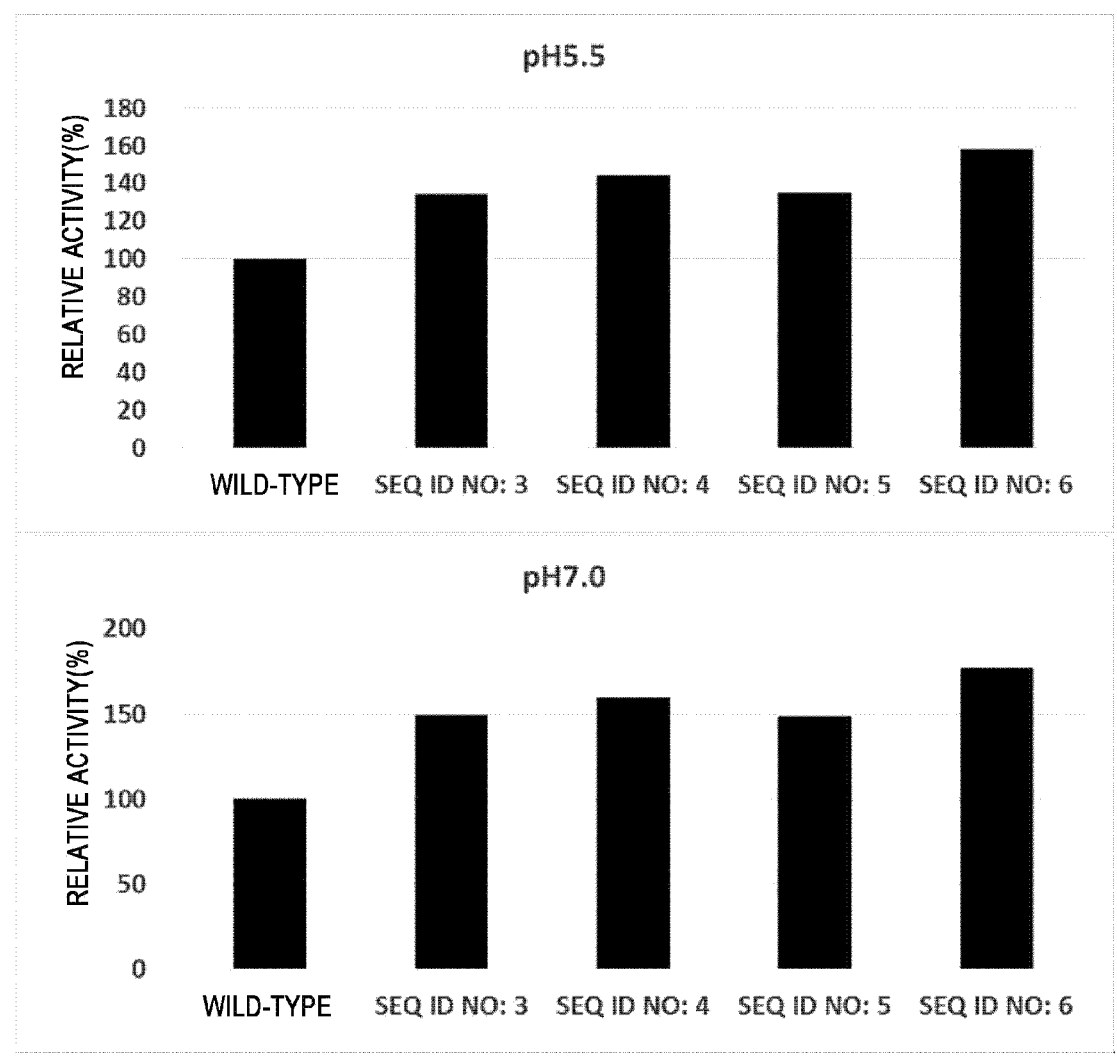

[Fig. 2]
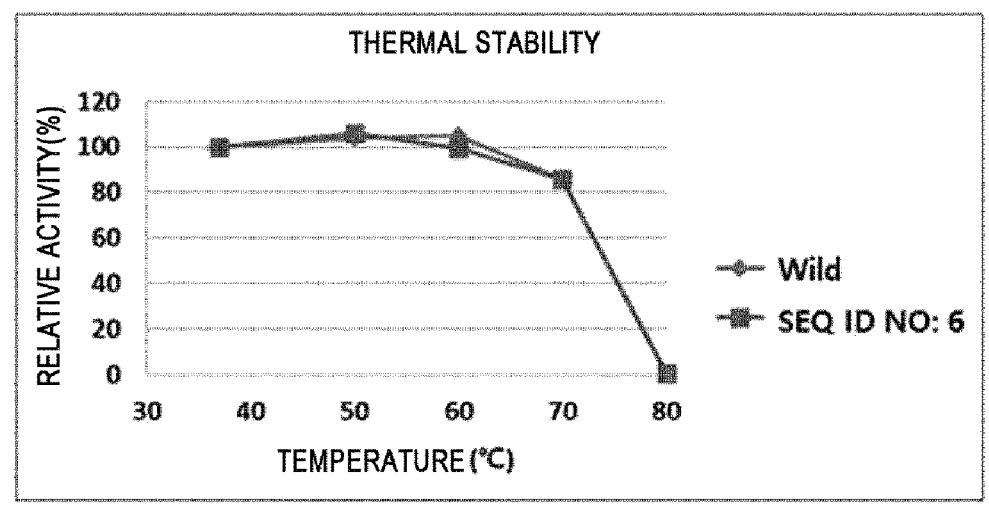

MODIFIED POLYPEPTIDE HAVING MANNANASE ACTIVITY

CROSS-REFERENCE TO RELATED APPLICATIONS

The present application is a 35 U.S.C. § 371 national-phase filing of International Application No. PCT/KR2022/010853, filed on Jul. 25, 2022, which claims the benefit of Korean Patent Application No. 10-2022-0011725, filed on Jan. 26, 2022, both of which applications are incorporated herein by reference in their entirety.

INCORPORATION BY REFERENCE

This application contains a sequence listing entitled "059520_00034_ST26.txt." being submitted herein in ASCII format via EFS-Web, which is a copy of the sequence listing as filed in PCT/KR2022/010853, which was modified on Aug. 8, 2022 and is 25,166 bytes in size.

TECHNICAL FIELD

The present disclosure relates to a modified polypeptide having mannanase activity and a use thereof.

BACKGROUND ART

Mannan polymers, as major constituent substances of hemicellulose, are classified into β-mannan, glucomannan, galactomannan, and galactoglucomannan according to a sugar component and β-1,4 bonds between sugars constituting a mannan polymer form a linear backbone. β-Mannan, present in nonleguminous plants including ivory nut, is a non-substituted linear polymer having a backbone formed of β-1,4-linked mannose. Glucomannan, present in konjac, is a polymer having a backbone in which β-1,4-linked mannose and glucose regularly alternate with each other. Galactomannan and galactoglucomannan are β-mannan and glucomannan, respectively, including α-galactose linked to O-6 of a mannose residue. Galactomannan is present in seeds of leguminous plants in large amounts, and acetylated galactoglucomannan is a major component of softwood.

β-D-Mannanase (mannan endo-1,4-beta-mannosidase; EC 3.2.1.78) is an endo-type hydrolytic enzyme having a property of randomly decomposing 1,4-β-D-mannan formed of galactomannan, glucomannan, galactoglucomannan, and mannan. Mannan is a component of various plant materials such as soybean, guar, alfalfa, palm kernel cake, and copra, which are known as anti-nutrient factors, and decomposition of mannan is essential in order to activate digestion and absorption thereof. Therefore, various types of mannanase are used as enzymes for animal feeds.

For absorption of nutrients after animals ingest animal feeds, the animal feeds need to be decomposed by various enzymes in the intestine in which the pH is neutral. However, application of mannanase to animal feeds is limited due to relatively low activity at a neutral pH. Therefore, the necessity has arisen for research on mannanase with enhanced activity under intestinal pH conditions.

RELATED ART DOCUMENT

Patent Document (Patent Document 1) KR 10-2016-0045465 A

DISCLOSURE

Technical Problem

The present inventors have found a modified polypeptide having mannanase activity and a use thereof, thereby completing the present disclosure.

Technical Solution

An object of the present disclosure is to provide a modified polypeptide having mannanase activity.

In an embodiment, the modified polypeptide consists of an amino acid sequence as set forth in one of SEQ ID NOS: 3 to 6.

Another object of the present disclosure is to provide a composition including the modified polypeptide of the present disclosure.

Another object of the present disclosure is to provide a composition for reaction with a mannan-containing substance, the composition including the modified polypeptide of the present disclosure.

Another object of the present disclosure is to provide a use of the modified polypeptide and/or the composition including the modified polypeptide for reaction with a mannan-containing substance.

Another object of the present disclosure is to provide a method for producing mannose, mannobiose, mannotriose, or long-chain mannooligosaccharides, the method including bringing a mannan-containing substance into contact with the modified polypeptide, a host cell expressing the modified polypeptide, and/or a composition including the modified polypeptide.

Another object of the present disclosure is to provide a method for decomposing a mannan-containing substance, the method including treating a substrate with the modified polypeptide, a host cell expressing the modified polypeptide, and/or a composition including the modified polypeptide.

Another object of the present disclosure is to provide a polynucleotide encoding the modified polypeptide.

Another object of the present disclosure is to provide a nucleic acid construct including the polynucleotide.

Another object of the present disclosure is to provide a vector including the polynucleotide or the nucleic acid construct.

Another object of the present disclosure is to provide a host cell including the modified polypeptide, the polynucleotide, the nucleic acid construct, and/or the vector.

Another object of the present disclosure is to provide a method for preparing a modified polypeptide, the method including: culturing the host cell; and recovering the modified polypeptide expressed in the culturing step.

Advantageous Effects

The modified polypeptide having mannanase activity of the present disclosure may be efficiently used in various industrial fields.

DETAILED DESCRIPTION OF PREFERRED EMBODIMENTS

Hereinafter, embodiments of the present disclosure will be described in detail. Meanwhile, each description and embodiment disclosed in the present disclosure may be applied to describe different descriptions and embodiments. In other words, all combinations of various components disclosed in the present disclosure are included within the scope of the present disclosure. Furthermore, the scope of the present disclosure should not be limited by the detailed description provided below.

Also, those skilled in the art will recognize or be able to ascertain, using no more than routine experimentation, many equivalents to specific embodiments of the present disclosure. Such equivalents are intended to be encompassed in the scope of the present disclosure.

As used in the specification and in the appended claims, the singular forms "a", "an", and "the" include plural references unless the context clearly dictates otherwise. Singular terms include the plural forms and plural terms include the singular form, unless otherwise stated. Throughout the specification and the appended claims of the present disclosure, the term "or" may be used to include "and/or", unless otherwise stated.

As used herein, the term "about" may be used in front of a particular numerical value. The term "about" used in the present disclosure is inclusive of not only the stated value following the term but also an acceptable range of deviation for the stated value. In consideration of the context in which the numerical value is provided, the acceptable range of deviation for the value may be determined. For example, the term "about" may refer to a range of −10% to +10% of a given numerical value. As another example, the term "about" may refer to a range of −5% to +5% of the numerical value. However, the present disclosure is not limited thereto.

As used herein, the terms "first, second, third . . . ", "i), ii), iii) . . . ", and "(a), (b), (c), (d) . . . ", etc. are used to distinguish similar components and do not imply that they are performed consecutively or sequentially. For example, when these terms are used with regard to steps of a method, use, or analysis, the steps may be performed without time intervals therebetween, may be performed concurrently, or may be performed at intervals of several seconds, minutes, hours, days, or months.

As used herein, the term "consisting essentially of" means that unspecified other components may be contained as long as characteristics imparted by the present disclosure are not substantially affected by the presence of the unspecified other components.

As used herein, the term "consisting of" means that the proportion of a specified component(s) is 100% in total. Components or characteristics following the term "consisting of" may be essential or obligatory. In some specified embodiments, other than the components or characteristics following the "consisting of", any components or non-essential components may be excluded.

As used herein, the term "comprising" refers to the presence of stated features, steps, or components following the term, but do not preclude the presence or addition of one or more other features, steps, or components. Although the components or characteristics following the term "comprising" may be essential or obligatory in the present disclosure, any other or non-essential components or characteristics may further be included in some specified embodiments.

As used herein, the term "comprising" may be modified to indicate "consisting essentially of" or "consisting of" in some specified embodiments.

With regard to an amino acid sequence in the present disclosure, although the expression a polypeptide "comprising" an amino acid sequence as set forth in a predetermined SEQ ID NO, a polypeptide "consisting of" an amino acid sequence as set forth in a predetermined SEQ ID NO, or a polypeptide or protein "having" an amino acid sequence as set forth in a predetermined SEQ ID NO is used, it is obvious that any protein including deletion, modification, substitution, conservative substitution, or addition of one or several amino acids may be used in the present disclosure as long as the protein has activity identical or equivalent to that of the polypeptide consisting of the amino acid sequence of the SEQ ID NO. For example, addition of a sequence not changing the function of the protein to the N-terminus and/or the C-terminus of the amino acid sequence, a naturally occurring mutation, a silent mutation thereof, or a conservative substitution thereof may be used, without being limited thereto.

As used herein, the term "protein" or "polypeptide" refers to a polymer or oligomer of consecutive amino acid residues. In the present disclosure, the polypeptide", "protein", or "peptide" may be used interchangeably with "amino acid sequence".

In some cases, an amino acid sequence exhibiting activity may be referred to as "enzyme". In the present disclosure, an amino acid sequence is written in an orientation from the N-terminus to the C-terminus, unless otherwise stated.

With regard to a cell, nucleic acid, polypeptide, or vector, the term "recombinant" used herein refers to the cell, nucleic acid, polypeptide, or vector modified by introduction of a heterologous nucleic acid or polypeptide or alteration of a native nucleic acid or polypeptide, or a cell, nucleic acid, polypeptide, or vector derived from the modified cell, nucleic acid, polypeptide, or vector. Thus, for example, a recombinant cell may express a gene that is not found within the native (non-recombinant) form of the cell or express native genes which are expressed or not expressed, or alternatively, abnormally expressed.

As used herein, the term "isolated" refers to a substance present in an environment which does not occur naturally or present in a form which does not exist naturally. This includes that a substance (sequence, enzyme, or nucleic acid) is at least substantially free from one or more other components including the substance (sequence, enzyme, or nucleic acid) which is naturally associated in nature and as found in nature.

For example, the isolated sequence, enzyme, or nucleic acid of the present disclosure may be provided in a form that is substantially free of one or more contaminants.

Examples of the isolated substance may include, i) any substance which is not naturally occurring, ii) any substance from which one or more naturally-occurring component associated in nature is removed (e.g., enzyme, variant, nucleic acid, protein, peptide, or cofactor), iii) any substance that has been artificially modified from a substance found in nature, or iv) a substance modified to change the amount of the substance compared to other components naturally associated therewith (e.g., by increasing the copy number of a gene encoding a particular substance; by modifying a promoter naturally associated with a gene encoding a particular substance with a stronger promoter, and the like, without being limited thereto.

As used herein, the term "wild-type" refers to naturally occurring without having artificial modification. When used in connection with a polypeptide, the term "wild-type" refers to a naturally occurring polypeptide that does not have artificial variation (substitution, insertion, deletion, or the like at one or more positions of amino acids. Similarly, when used in connection with a polynucleotide, the term "wild-type" refers to a polynucleotide not having artificial modification (substitution, insertion, or deletion) of one or more nucleotides. However, the polynucleotide encoding the wild-type polypeptide is not limited to natural polynucleotides but includes any sequence encoding the wild-type polypeptide.

In the present disclosure, parent sequence or backbone refers to a reference sequence into which modification is introduced to produce a modified polypeptide. That is, the parent sequence may be a target as a starting sequence into which mutation such as substitution, insertion, and/or deletion is introduced. The parent sequence may be a naturally occurring or wile-type sequence, a variant having at least one of substitution, insertion, or deletion occurs in the naturally occurring or wild-type sequence, or an artificially synthesized sequence. When the parent sequence is an amino acid sequence exhibiting activity, i.e., an amino acid sequence of an enzyme, it may be referred to as a parent enzyme.

As used herein, the term "reference sequence" refers to a sequence used to determine a position of an amino acid in an amino acid sequence. A position of an amino acid in any amino acid sequence corresponding to a particular position in the reference sequence may be determined by aligning the amino acid sequence and the reference sequence.

With regard to the amino acid sequence or nucleic acid sequence, the term "fragment" refers to a part of a parent sequence. For example, the fragment may be a polypeptide from which at least one amino acid is removed from the C-terminus or the N-terminus of the parent sequence.

As used herein, the term "fragment" of an enzyme may refer to a "functional fragment". The "functional fragment" may also be referred to as active fragment and indicates a polypeptide, as a part of a parent enzyme, having the activity of the parent enzyme. For example, the functional fragment of the enzyme may include a catalytic site of the enzyme.

The fragment of the enzyme may include a part of the full length of a parent enzyme. For example, the fragment of the enzyme may include at least about 20%, 30%, 40%, 50%, 60%, 70%, 80%, 90%, 95%, 98%, 99% or more and less than 100% of amino acids of the full length of the parent enzyme.

In the present disclosure, the "varying/modifying" refers to changing or altering. This may be alteration from naturally occurring. For example, an enzyme may be changed by altering the parent sequence or reference sequence of the enzyme.

In the present disclosure, the modified enzyme may be an enzyme not existing in nature, i.e., an enzyme which does not occur naturally.

As used herein, the term "modified" refers to, for example, altered from a naturally occurring form. A modified enzyme of the present disclosure includes an enzyme which does not occur naturally or a naturally occurring variant. For example, the modified enzyme of the present disclosure is an enzyme not found in nature. For example, the modified enzyme of the present disclosure may not be a spontaneously occurring enzyme, without being limited thereto.

When used in connection with an amino acid/nucleic acid sequence, the term "modification" used herein may include substitution of an amino acid/nucleic acid residue at one or more site of a parent sequence with a different amino acid/nucleic acid residue, deletion of an amino acid/nucleic acid residue (or a series of amino acid/nucleic acid residues) of the parent sequence at one or more sites, insertion of an amino acid/nucleic acid residue (or a series of amino acid/ nucleic acid residues) into the parent sequence at one or more sites, truncation of an amino acid sequence of the N-terminus and/or the C-terminus or a 5' and/or 3' nucleic acid sequence, and any combination thereof.

In the present disclosure, the "variant" or "modified polypeptide" of an enzyme refers to a protein including at least one different amino acid from that of a parent enzyme by conservative substitution and/or modification. The "variant" and the "modified polypeptide" may be used interchangeably. The variant or modified polypeptide may be one which does not occur naturally, without being limited thereto.

The variant has a sequence different from that of the parent enzyme by modification such as substitution, deletion, and/or insertion of amino acids.

Such variants may generally be identified by modifying one or more amino acids in the parent enzyme and evaluating properties of the modified protein. That is, the ability of the variant may be enhanced, unchanged, or diminished relative to that of the parent enzyme.

In addition, some variants may include modified polypeptides from which one or more parts, such as an N-terminal leader sequence or transmembrane domain, have been removed.

Other variants may include those from which a part of the N- and/or C-terminus of a mature protein.

The term "variant" or "modified polypeptide" may be interchangeably used with modification, modified protein, mutant, mutein, divergent, and the like, without limitation, as long as the terms are used to indicate variation.

A variant may also include deletion or addition of amino acids that have minimal influence on properties and a secondary structure of the polypeptide. For example, the polypeptide may be conjugated with a signal (or leader) sequence at the N-terminus of a protein which co-translationally or post-translationally directs transfer of the protein. The polypeptide may also be conjugated with another sequence or linker for identification, purification, or synthesis of the polypeptide.

For example, the variant conjugated with the signal (or leader) sequence at the N-terminus of a protein which co-translationally or post-translationally directs transfer of the protein may be, but is not limited to, a polypeptide of SEQ ID NO: 7. Also, the variant may be a polypeptide having at least about 60%, 70%, 75%, 80%, 85%, 90%, 95%, 96%, 97%, 98%, or 99% sequence homology with the polypeptide of SEQ ID NO: 7 as long as the polypeptide has mannanase activity, and any polypeptide having activity identical or equivalent to that of the polypeptide consisting of the amino acid sequence of SEQ ID NO: 7 may be included in the range of variants conjugated with the signal (or leader) sequence of the N-terminus of the protein.

In addition, a polynucleotide encoding the variant conjugated with the signal (or leader) sequence at the N-terminus of the protein may include a nucleotide sequence encoding the amino acid sequence as set forth in SEQ ID NO: 7. In an embodiment of the present disclosure, the polynucleotide may have or include a sequence of SEQ ID NO: 8. In addition, the polynucleotide may consist of or consist essentially of the sequence of SEQ ID NO: 8. Specifically, the polynucleotide may have or include a nucleotide sequence having a homology or identity of 70% or more, 75% or more, 80% or more, 85% or more, 90% or more, 95% or more, 96% or more, 97% or more, 98% or more, and less than 100% with the sequence of SEQ ID NO: 8, or may consist of or consist essentially of a nucleotide sequence having a homology or identity of 70% or more, 75% or more, 80% or more, 85% or more, 90% or more, 95% or more, 96% or more, 97% or more, 98% or more, and less than 100% with the sequence of SEQ ID NO: 8.

As used herein, the term "conservative substitution" refers to substitution of one amino acid with a different amino acid having a similar structural and/or chemical property. Such amino acid substitution may generally occur based on similarity of polarity, charge, solubility, hydrophobicity, hydrophilicity, and/or amphipathic nature of a residue.

Throughout the specification, the conventional one-letter and three-letter codes for naturally occurring amino acids are used. In addition, the amino acids mentioned herein are abbreviated according to the nomenclature rules of IUPAC-IUB as follows.

| alanine | Ala, A | arginine | Arg, R |
| asparagine | Asn, N | aspartic acid | Asp, D |
| cysteine | Cys, C | glutamic acid | Glu, E |
| glutamine | Gln, Q | glycine | Gly, G |
| histidine | His, H | isoleucine | Ile, I |
| leucine | Leu, L | lysine | Lys, K |
| methionine | Met, M | phenylalanine | Phe, F |
| proline | Pro, P | serine | Ser, S |
| threonine | Thr, T | tryptophan | Trp, W |
| tyrosine | Tyr, Y | valine | Val, V |

Meanwhile, any amino acid may be described as Xaa, X.

Also, three-letter codes generally allowed for other amino acids, such as 2-aminoisobutyric acid (Aib), N-methylglycine (Sar), and α-methyl-glutamic acid, may be used as well as the naturally occurring amino acids.

Amino acids may generally be classified based on similarity of polarity, charge, solubility, hydrophobicity, hydrophilicity, and/or amphipathic nature of a residue. Thus, amino acid substitution may generally occur based on similarity of polarity, charge, solubility, hydrophobicity, hydrophilicity, and/or amphipathic nature of a residue.

For example, among electrically charged amino acids with side chains, positively charged (basic) amino acids include arginine, lysine, and histidine and negatively charged (acidic) amino acids include glutamic acid and aspartic acid; and among uncharged amino acids with side chains, nonpolar amino acids include glycine, alanine, valine, leucine, isoleucine, methionine, phenylalanine, tryptophan, and proline, and polar or hydrophilic amino acids include serine, threonine, cysteine, tyrosine, asparagine, and glutamine. Among the nonpolar amino acids, aromatic amino acids include phenylalanine, tryptophan, and tyrosine.

As used herein, the term "gene" refers to a polynucleotide encoding a polypeptide and a polynucleotide including regions upstream and downstream of the coding region. In an embodiment, the gene may have a sequence (intron) inserted between coding regions (exons).

As used herein, the term "homology" or "identity" refers to the degree of relatedness between two given amino acid sequences or nucleotide sequences and may be expressed as a percentage. The terms homology and identity may often be used interchangeably.

Sequence homology or identity of conserved polynucleotides or polypeptides may be determined by standard alignment algorithm and default gap penalties established by a program may be used together therewith. Substantially, homologous or identical sequences may generally hybridize with each other at least about 50%, 60%, 70%, 80% or 90% of the entire sequence or the full length under moderate or highly stringent conditions. It is obvious that polynucleotides including general codon or degenerated codon is also included in hybridization.

The homology, similarity, or identity between two polynucleotide or polypeptide sequences may be determined using any computer algorithm known in the art, such as "FASTA" program, using default parameters introduced by Pearson et al. (1988) *Proc. Natl. Acad. Sci. USA* 85:2444. Alternatively, the homology, similarity, or identity may be determined using the Needleman-Wunsch algorithm (Needleman and Wunsch, 1970, *J. Mol. Biol.* 48:443-453) as implemented in the Needleman program of the EMBOSS package (EMBOSS: The European Molecular Biology Open Software Suite, Rice et al., 2000, *Trends Genet.* 16:276-277) (version 5.0.0 or later) (including GCG program package (Devereux, J., et al., *Nucleic Acids Research* 12:387 (1984)), BLASTP, BLASTN, FASTA (Atschul, S. F. et al., *J MOLEC BIOL* 215:403 (1990); Guide to Huge Computers, Martin J. Bishop, ed., Academic Press, San Diego, 1994, and CARILLO et al. (1988) *SIAM J Applied Math* 48:1073). For example, the homology, similarity, or identity may be determined using BLAST, from the National Center for Biotechnology Information database, or ClustalW.

The homology, similarity, or identity between polynucleotides or polypeptides may be determined by comparing sequence information using a GAP computer program as introduced by Needleman et al., (1970), *J Mol Biol.* 48:443 as disclosed by Smith and Waterman, *Adv. Appl. Math* (1981) 2:482. Briefly, the GAP program defines similarity as the number of aligned symbols (i.e., nucleotides or amino acids) which are similar, divided by the total number of symbols in a shorter of two sequences. Default parameters for the GAP program may include: (1) a binary comparison matrix (containing a value of 1 for identities and 0 for non identifies) and a weighted comparison matrix of Gribskov, et al. (1986), *Nucl. Acids Res.* 14:6745 as described by Schwartz and Dayhoff, eds., *Atlas Of Protein Sequence and Structure*, National Biomedical Research Foundation, pp. 353-358 (1979) (or EDNAFULL (EMBOSS version of NCBI NUC4.4) substitution matrix); (2) a penalty of 3.0 for each gap and an additional penalty of 0.10 for each symbol in each gap (or a gap open penalty of 10 and a gap extension penalty of 0.5); and (3) no penalty for end gaps.

Also, the sequence homology, similarity, or identity between two given polynucleotides or polypeptides may be identified by comparing sequences thereof by southern hybridization under defined stringent conditions, and the defined stringent hybridization conditions are within the scope of the technology and may be defined by a method well known to one of ordinary skill in the art (e.g., J. Sambrook et al., *Molecular Cloning, A Laboratory Manual*, 2nd Edition, Cold Spring Harbor Laboratory press, Cold Spring Harbor, New York, 1989; F. M. Ausubel et al., *Current Protocols in Molecular Biology*, John Wiley & Sons, Inc., New York), without being limited thereto.

As used herein, the term "mature polypeptide" refers to a polypeptide in its final form not including a signal sequence or a propeptide sequence. Mature protein/polypeptide/peptide may functional be forms of the protein/polypeptide/peptide. The mature polypeptide may be in the final form following translation and any post-translational modification. Examples of the post-translational modification may include N-terminal or C-terminal modification, glycosylation, phosphorylation, removal of a leader sequence, and the like, without being limited thereto.

As used herein, the term "nucleic acid construct" refers to a nucleic acid molecule, either single- or double-stranded, including at least one regulatory sequence and artificially synthesized, modified to include a particular sequence in a manner that would not otherwise exist in nature, or isolated from a naturally occurring gene.

As used herein, the term "expression" includes any process involved in production of a polypeptide such as transcription, post-transcriptional modification, translation, post-translational modification, and secretion, without being limited thereto.

As used herein, the term "expression vector" refers to a linear or circular nucleic acid molecule including a coding sequence and an operably linked regulatory sequence for expression thereof.

As used herein, the term "operably linked" refers to binding of a regulatory sequence to an appropriate position to regulate expression of a coding sequence. Therefore, the "operably linked" includes binding between a regulatory region of a functional domain having a known or desired activity such as a promoter, a stop codon, a signal sequence, or an enhancer and a target (gene or polypeptide) to regulate expression, secretion, or function of the target in accordance with the known or desired activity.

As used herein, the term "cDNA" refers to a DNA sequence that may be prepared by reverse transcription from a mature, spliced mRNA molecule obtained from eukaryotic or prokaryotic cells. The cDNA sequence does not include an intron sequence that may be present in the corresponding genomic DNA. The initial primary RNA transcript is a precursor of mRNA that is processed through a series of steps, including splicing, before appearing as mature spliced mRNA.

As used herein, the term "regulatory sequence" refers to a polynucleotide sequence required for expression of a coding sequence. Each regulatory sequence may be native (from the same gene) or foreign (from different gene) to the coding sequence. Examples of the regulatory sequence include a leader sequence, a polyadenylation sequence, a propeptide sequence, a promoter, a signal peptide sequence, an operator sequence, a ribosome binding site-encoding sequence, and a sequence terminating transcription and translation. A minimum unit of the regulatory sequence may include a promoter and a sequence terminating transcription and translation.

As used herein, the term "corresponding to" refers to an amino acid residue at a position cited in a protein or polypeptide or an amino acid residue similar, identical, or homologous to the residue cited in the protein or polypeptide. Identifying the amino acid at the corresponding position may be determining a specific amino acid in a sequence referring to a specific sequence. As used herein, the "corresponding region" generally refers to a region similar or corresponding thereto in a related protein or a reference protein.

For example, an arbitrary amino acid sequence is aligned with SEQ ID NO: 1 and then each amino acid residue of the amino acid sequence may be numbered with reference to the position of each corresponding amino acid residue of SEQ ID NO: 1. For example, positions of amino acids or positions where substitution, addition, or deletion occurs may be identified using a sequence alignment algorithm as disclosed herein by comparison with query sequence (also, "reference sequence").

Such alignment may be conducted using, for example, the Needleman-Wunsch algorithm (Needleman and Wunsch, 1970, *J. Mol. Biol.* 48:443-453), a Needle program of the EMBOSS package (EMBOSS: The European Molecular Biology Open Software Suite, Rice et al., 2000, *Trends Genet.* 16:276-277), without being limited thereto.

In addition, an amino acid residue corresponding to mannanase may be identified by multiple sequence alignment. Examples of the multiple sequence alignment program known in the art may include MUSCLE (multiple sequence comparison by log-expectation; version 3.5 or later; Edgar, 2004, *Nucleic Acids Research* 32:1792-1797), MAFFT (version 6.857 or later; Katoh and Kuma, 2002, *Nucleic Acids Research* 30:3059-3066; Katoh et al., 2005, *Nucleic Acids Research* 33:511-518; Katoh and Toh, 2007, *Bioinformatics* 23:372-374; Katoh et al., 2009, *Methods in Molecular Biology* 537:39-64; Katoh and Toh, 2010, *Bioinformatics* 26:1899-1900), and EMBOSS EMMA using ClustalW (1.83 or later; Thompson et al., 1994, *Nucleic Acids Research* 22:4673-4680), using respective default parameters thereof, without being limited thereto.

When relationship between enzymes derived from the mature polypeptide of SEQ ID NO: 1 cannot be detected by conventional sequence-based comparison, other pairwise sequence comparison algorithms may be used (Lindahl and Elofsson 2000, *J. Mol. Biol.* 295:613-615). Higher sensitivity in sequence-based searching may be obtained using search programs using probabilistic representations of polypeptide families (profiles) to search database. For example, PSI-BLAST program generates profiles through an iterative database search process and may detect remote homologs (Atschul et al., 1997, *Nucleic Acids Res.* 25:3389-3402). Even high sensitivity may be obtained when the family or superfamily for the polypeptide has one or more representatives in the protein structure database. Programs such as GenTHREADER (Jones, 1999, *J. Mol. Biol.* 287:797-815; and McGuffin and Jones, 2003, *Bioinformatics* 19:874-881) utilize information from a variety of sources, such as PSI-BLAST, secondary structure prediction, structural alignment profiles, and solvation potentials, as input to a neural network that predicts the structural folding for a query sequence. Similarly, a method introduced by Gough et al., 2000, *J. Mol. Biol.* 313:903-919 may be used to align a sequence of an unknown structure with the superfamily models present in the SCOP database. These alignments may be used in turn to generate a homology model for the polypeptide, and the models may be assessed for accuracy using a variety of tools developed for that purpose.

For proteins of known structures, several tools and resources are available for retrieving and generating structural alignment. For example, the SCOP superfamilies of proteins have been structurally aligned, and those alignments are accessible and downloadable. Two or more protein structures may be aligned using a variety of algorithms such as the distance alignment matrix (Holm and Sander, 1998, *Proteins* 33:88-96) or combinatorial extension (CE, Shindyalov and Bourne, 1998, *Protein Engineering* 11:739-747). Implementation of these algorithms may additionally be utilized to query structure databases with a structure of interest in order to discover possible structural homologs (Holm and Park, 2000, *Bioinformatics* 16:566-567).

The above-described methods are merely examples, and the present disclosure is not limited thereto.

Hereinafter, embodiments of the present disclosure will be described in more detail.

In the present disclosure, mannanase refers to an endo-type hydrolytic enzyme having a property of randomly decomposing 1,4-β-D-mannan in mannan. For example, mannanase may be β-D mannanase (mannan endo-1,4-beta-mannosidase). For example, mannanase may be an enzyme with an EC number of 3.2.1.78, but is not limited thereto. In the present disclosure, the mannanase may be used interchangeably with "β-D mannanase" and "endo-1,4-beta-mannosidase".

In the present disclosure, the activity of mannanase includes the aspect defined in the present disclosure and may be measured and evaluated using any method known in the art.

In the present disclosure, a "parent mannanase" refers to mannanase modified to produce the variant or modified polypeptide of the present disclosure. Specifically, the parent mannanase, parent enzyme, or parent sequence may be a naturally occurring polypeptide or wild-type polypeptide, or a mature polypeptide thereof, and may include a variant or a functional fragment thereof, but is not limited thereto as long as they have mannanase activity and may be used as a parent of the variant.

The parent mannanase provided in the present disclosure may be, but is not limited to, a polypeptide having SEQ ID NO: 1. Also, the parent mannanase may be a polypeptide having at least about 60%, 70%, 75%, 80%, 85%, 90%, 95%, 96%, 97%, 98%, or 99% sequence homology with the polypeptide of SEQ ID NO: 1 as long as the polypeptide has mannanase activity, and any polypeptide having activity identical or equivalent to that of the polypeptide consisting of the amino acid sequence of SEQ ID NO: 1 may be included in the range of parent mannanase.

A polynucleotide encoding the parent mannanase may include a nucleotide sequence encoding the amino acid sequence as set forth in SEQ ID NO: 1. In an embodiment of the present disclosure, the polynucleotide may have or include a sequence of SEQ ID NO: 2. Also, the polynucleotide may consist of or consist essentially of the sequence of SEQ ID NO: 2.

Various modifications may be made in the coding region of the polynucleotide of the present disclosure provided that they do not change the amino acid sequence of the parent mannanase of the present disclosure in consideration of codon degeneracy or codons preferred by an organism in which the parent mannanase of the present disclosure is to be expressed. Specifically, the polynucleotide may have or include a nucleotide sequence having a homology or identity of 70% or more, 75% or more, 80% or more, 85% or more, 90% or more, 95% or more, 96% or more, 97% or more, 98% or more, and less than 100% with the sequence of SEQ ID NO: 2, or may consist of or consist essentially of a nucleotide sequence having a homology or identity of 70% or more, 75% or more, 80% or more, 85% or more, 90% or more, 95% or more, 96% or more, 97% or more, 98% or more, and less than 100% with the sequence of SEQ ID NO: 2.

The parent mannanase of the variant provided in the present disclosure may be derived from the genus *Aspergillus*. Specifically, the parent mannanase may be derived from *Aspergillus niger*.

Meanwhile, the above-described microorganism is an example of microorganisms from which the parent mannanase is derived and includes any microorganisms taxonomically homologous therewith regardless of names of the microorganisms.

The above-described microorganism may be purchased from known microbial depository institutions such as ATCC, DSMZ, CBS, NRRL, KCTC, and KCCM.

In the present disclosure, a sequence "derived from" a particular microorganism is not limited to those naturally produced or producible but includes any sequence encoded by a gene which is produced in the microorganism including the gene and isolated therefrom.

For example, mannanase derived from the genus *Aspergillus* includes not only an enzyme naturally produced in *Aspergillus* and having mannanase activity, but also those produced in an *Aspergillus* source and those produced in other host cells by genetic modification (e.g., transformation with a sequence encoding the enzyme) known in the art.

In the present disclosure, the "modified polypeptide having mannanase activity" may be a variant of the parent mannanase.

As used herein, the term "variant of the parent mannanase" or "mannanase variant" refers to a protein having mannanase activity and at least one amino acid different from that of the amino acid sequence of the parent mannanase.

The "modified polypeptide having mannanase activity", "variant of the parent mannanase", and "mannanase variant" may be used interchangeably.

The variant provided in the present disclosure may include modification of at least one amino acid in the sequence of the parent mannanase while having the mannanase activity. In addition, i) the variant may be a polypeptide having a sequence identity of 70% or more and less than 100% with SEQ ID NO: 1; and/or ii) the modified polypeptide may be a polypeptide encoded by a polynucleotide having a sequence identity of 70% or more and less than 100% with a sequence encoding a mature polypeptide of SEQ ID NO: 1; and/or iii) the modified polypeptide may be a polypeptide encoded by a polynucleotide hybridized with (a) a sequence encoding a mature polypeptide of SEQ ID NO: 1, (b) cDNA thereof, or (c) a full-length complementary sequence of (a) or (b), under low-stringency conditions, medium-stringency conditions, medium-high-stringency conditions, high-stringency conditions, or very-high-stringency conditions; and/or iv) the modified polypeptide may be a functional fragment of the polypeptide i), ii), or iii) having the mannanase activity.

Specifically, the variant provided in the present disclosure may be one having at least one modified function or property compared to that of the parent mannanase by including modification of at least one amino acid in the sequence of the parent mannanase, while having the mannanase activity.

Specifically, the variant of the present disclosure may have at least one modified function or property compared to that of the parent mannanase by including modification of at least one amino acid in the sequence of the parent mannanase while having the mannanase activity, and may include at least one conservative substitution.

The variant provided in the present disclosure, as a variant of the parent mannanase, may be a polypeptide having the mannanase activity.

In an embodiment, the variant provided in the present disclosure may consist of an amino acid sequence as set forth in one of SEQ ID NOS: 3 to 6.

According to any one of the above-described specific embodiments, the variant of the present disclosure may have and/or include an amino acid sequence as set forth in SEQ ID NO: 3, 4, 5, or 6, or may consist essentially of or consist of the amino acid sequence.

According to any one of the above-described specific embodiments, the variant of the present disclosure may include at least 70%, 75%, 80%, 85%, 90%, 95%, 96%, 97%, 98%, 99%, 99.5%, 99.7%, or 99.9% homology or identity with the amino acid sequence as set forth in SEQ ID NO: 3, 4, 5, or 6. In addition, it is obvious that any polypeptide having an amino acid sequence including deletion, modification, substitution, conservative substitution, or addition of one or several amino acids may also be included within the range of the present disclosure as long as the polypeptide has such homology or identity and exhibiting the effect corresponding to that of the variant of the present disclosure.

In an embodiment, the variant provided in the present disclosure may be a variant conjugated with a signal (or leader) sequence of the N-terminus of a protein which co-translationally or post-translationally directs transfer of the protein. The "variant conjugated with a signal (or leader) sequence at the N-terminus of a protein" is as described above.

SEQ ID NO: 7 may be used as a reference sequence in determination of a position of an amino acid in the amino acid sequence of the variant conjugated with a signal (or leader) sequence of the N-terminus of the protein.

The variant provided in the present disclosure may be those in which a selectable or detectable property or attribute of a polypeptide is changed compared to other mannanase, e.g., wild-type mannanase, parent mannanase, and other mannanase variants.

The property or attribute includes, but is not limited to, oxidative stability, substrate specificity, catalytic activity, thermal stability, alkaline stability, pH activity profile, resistance to proteolytic degradation, $K_m$, $K_{cat}$, $K_{cat}/K_m$ ratios, protein folding, induction of immune response, ability to bind to a ligand, ability to bind to a receptor, ability to be secreted, ability to be displayed on the surface of a cell, ability to form an oligomer, ability to transmit a signal, ability to promote cell proliferation, ability to induce apoptosis, ability to be refined by phosphorylation or glycosylation, and/or ability to treat a disease.

Specifically, the variant provided in the present disclosure may have enhanced thermal tolerance and/or thermal stability compared to the parent sequence. For example, the modified polypeptide of the present disclosure may have enhanced thermal tolerance and/or thermal stability compared to the polypeptide consisting of the amino acid sequence of SEQ ID NO: 1, without being limited thereto.

Specifically, the variant provided in the present disclosure may have enhanced enzymatic activity, compared to the parent sequence, at a pH of 5.0 to 9.0, at a pH of 5.0 to 8.0, at a pH of 5.0 to 7.5, or at a pH of 5.5 to 7.0. That is, the variant provided in the present disclosure may efficiently obtain hydrolysates due to high enzymatic activity in the intestinal pH ranges of animals. For example, the modified polypeptide of the present disclosure may have enhanced enzymatic activity in the pH range of 5.0 to 9.0 compared to the polypeptide consisting of the amino acid sequence of SEQ ID NO: 1, without being limited thereto.

In the present disclosure, the "enzymatic activity" indicates at least one catalytic activity. Specifically, the enzymatic activity may be a conversion ratio of an enzyme mainly expressed as $K_{cat}/K_m$, but is not limited thereto.

The $K_{cat}$ refers to a catalytic constant for conversion of a substrate into a product within a unit time by an enzyme when the enzyme is completely saturated with the substrate and may also be referred to as a turnover number. The $K_m$ is a substrate concentration when a reaction rate is half the peak value ($V_{max}$).

As an example of expressing the enzymatic activity, specific activity (μmol of converted substrate×mg$^{-1}$×min$^{-1}$) or volumetric activity (μmol of converted substrate×mL$^{-1}$×min$^{-1}$) may be used.

However, definition of the enzymatic activity is not limited to those given above, but may be defined and evaluated based on contents introduced by Irwin H. Segel, *Enzyme kinetics*, John Wiley & Sons, 1979; A. G. Marangoni, *Enzyme kinetics*, Wiley-Interscience, 2003; A. Fersht, *Enzyme structure and mechanisms*, John Wiley & Sons, 1981; *Structure and Mechanism in Protein Science: A guide to enzyme catalysis and protein folding*, Alan Fersht, W. H. Freeman, 1999; *Fundamentals of Enzyme Kinetics*, Athel Cornish-Bowden, Wiley-Blackwell 2012; and Voet et al., Biochemie [Biochemistry], 1992, VCH-Verlag, Chapter 13, pages 331-332 with respect to enzymatic activity.

In an embodiment, the variant provided in the present disclosure may have enzymatic activity enhanced by about 100%, about 110%, about 120%, about 130%, about 140%, about 150%, about 160%, about 170%, about 171%, about 172%, about 173%, about 174%, about 175%, about 176%, about 177% or about 180% or more compared to the parent enzyme. As one of those examples given above, the parent enzyme may be a polypeptide represented by SEQ ID NO: 1.

As used herein, the term "specific activity" is the activity of an enzyme per unit weight of a protein and may be expressed as unit/mg. Proteins may be quantified, for example, using SDS-PAGE or Bradford assay.

Enzyme stability means that enzymatic activity is maintained during storage or reaction time. For measurement of changes in the stability, the degree of loss of the enzymatic activity or enzyme stability may be expressed by measuring initial enzymatic activity under preset conditions at time zero (100%) and enzymatic activity after a certain period of time (x %) and comparing the measured values.

Factors affecting enzymatic activity may be, for example, pH, heat, and presence of other substances (e.g., oxidizer and chelating agent).

As used herein, the term "pH stability" refers to the ability of a protein to function in a particular pH range. In the case where the function of the protein is maintained in the particular pH range, the protein may be defined as having "pH stability". In an embodiment, the variant provided in the present disclosure may have high enzymatic activity in the pH range of pH 5.0 to pH 9.0, pH 5.5 to pH 8.0, pH 5.0 to pH 7.5, or pH 5.5 to pH 7.0, but is not limited thereto.

As used herein, the term "thermal stability" refers to the ability of a protein to function in a particular temperature range. In an embodiment, the variant provided in the present disclosure may have activity in a temperature range of about 25° C. to about 100° C., but is not limited thereto.

As used herein, the term "thermal tolerance" refers to the ability of a protein to function at a particular temperature, e.g., at a high temperature or at an extremely low temperature. For example, a protein having thermal tolerance may not function at a temperature to which the protein is exposed but may function when returns to an optimal temperature environment.

Enhancement of stability may include maintaining high enzymatic activity, increases in ranges of pH, temperature, and/or time in which the function of the protein is maintained, compared to other enzymes, e.g., wild-type enzyme, parent enzyme, and/or other variants.

Enhancement of stability may include maintaining low enzymatic activity, decreases in ranges of pH, temperature, and/or time in which the function of the protein is maintained, compared to other enzymes, e.g., wild-type enzyme, parent enzyme, and/or other variants.

As used herein, the term "substrate specificity" refers to the ability of an enzyme to identify a substrate and molecules competing the substrate. The substrate specificity may be determined by measuring the activity of an enzyme on different substrates. In an embodiment, alteration in substrate specificity may be a change of specificity to a substrate capable of producing a target product in an increasing direction. As another example, alteration in substrate specificity may be a change of specificity to a substrate capable of producing a target product in a decreasing direction.

Modified properties of the variant provided in the present disclosure may be appropriate or improved activity applicable to various industrial fields including animal feeds, baking, pulp bleaching, and the like.

The polynucleotide encoding the variant of the present disclosure may include a coding sequence of the above-described variant. In the polynucleotide, various modifications may be made in the coding region provided that they do not change the amino acid sequence of the polypeptide due to codon degeneracy or in consideration of a codon preferred by an organism in which the protein is to be expressed.

Also, the polynucleotide of the present disclosure may include any nucleotide sequence that is hybridized with a probe constructed using known gene sequences, e.g., a nucleotide sequence entirely or partially complementary to the nucleotide sequence under stringent conditions to encode the variant of the present disclosure, without limitation.

The term "stringent conditions" refers to conditions which permit specific hybridization between polynucleotides. Such conditions are disclosed in detail in known documents (e.g., J. Sambrook et al., *Molecular Cloning, A Laboratory Manual*, 2nd Edition, Cold Spring Harbor Laboratory press, Cold Spring Harbor, New York, 1989; F. M. Ausubel et al., *Current Protocols in Molecular Biology*, John Wiley & Sons, Inc., New York).

For example, the conditions may include performing hybridization between polynucleotides having a high homology or identity, e.g., a homology or identity of 40% or more, specifically 90% or more, more specifically 95% or more, 96% or more, 97% or more, 98% or more, even more specifically 99% or more, without performing hybridization between polynucleotides having a homology or identity lower than the above homologies or identities, or performing hybridization once, specifically two or three times, under conventional washing conditions for Southern hybridization at a salt concentration and temperature of 60° C., 1×SSC, and 0.1% SDS, specifically 60° C., 0.1×SSC, and 0.1% SDS, and more specifically 68° C., 0.1×SSC, and 0.1% SDS.

Hybridization requires that two nucleic acids have complementary sequences, although bases may mismatch due to the degree of stringency of hybridization. The term "complementary" is used to describe the relationship between bases of nucleotides capable of hybridizing with each other. For example, with respect to DNA, adenine is complementary to thymine, and cytosine is complementary to guanine. Thus, the polynucleotide of the present disclosure may include not only substantially similar nucleic acid sequences but also nucleic acid fragments isolated but complementary to the entire sequence.

Particularly, the polynucleotide having homology or identity may be detected under hybridization conditions including a hybridization step using 55° C. as a $T_m$ value using the above-described conditions. Also, the $T_m$ value may be 60° C., 63° C., or 65° C., but is not limited thereto, and may be appropriately adjusted by those skilled in the art according to the purpose.

An appropriate degree of stringency for hybridizing polynucleotides may depend on lengths of the polynucleotides and degrees of complementarity and parameters are well known in the art (Sambrook et al., supra, 9.50-9.51, 11.7-11.8).

For example, the "high-stringency condition" occurs at about 5° C. to 10° C. below the $T_m$ of a probe, the "medium-stringency condition" occurs at about 10° C. to 20° C. below the $T_m$ of the probe, and the "low-stringency condition" occurs at about 20° C. to 25° C. below the $T_m$ of a probe, without being limited thereto.

For example, the "low-stringency condition" means a condition allowing prehybridization and hybridization with probes of at least 100 nucleotides in length at 42° C. in 5×SSPE, 0.3% SDS, 200 μg/mL sheared and denatured salmon sperm DNA, and 25% formamide, according to standard Southern blotting procedures for 12 to 24 hours. The carrier material is finally washed twice to three times each for 15 minutes using 2×SSC and 0.1% to 0.2% SDS at 50° C.

For example, the "medium-stringency condition" means a condition allowing prehybridization and hybridization with probes of at least 100 nucleotides in length at 42° C. in 5×SSPE, 0.3% SDS, 200 μg/mL sheared and denatured salmon sperm DNA, and 35% formamide, according to standard Southern blotting procedures for 12 to 24 hours. The carrier material may be finally washed twice to three times each for 15 minutes using 2×SSC and 0.1% to 0.2% SDS at 55° C. For example, the "medium-high-stringency condition" means a condition allowing prehybridization and hybridization with probes of at least 100 nucleotides in length at 42° C. in 5×SSPE, 0.3% SDS, 200 μg/mL sheared and denatured salmon sperm DNA, and 35% formamide, according to standard Southern blotting procedures for 12 to 24 hours. The carrier material is finally washed twice to three times each for 15 minutes using 1× to 2×SSC and 0.1 to 0.2% SDS at 60° C.

For example, the "high-stringency condition" means a condition allowing prehybridization and hybridization with probes of at least 100 nucleotides in length at 42° C. in 5×SSPE, 0.3% SDS, 200 μg/mL sheared and denatured salmon sperm DNA, and 35% formamide, according to standard Southern blotting procedures for 12 to 24 hours. The carrier material may be finally washed twice to three times each for 15 minutes using 2×SSC and 0.1% to 0.2% SDS at 65° C.

The nucleic acid construct provided in the present disclosure includes a polynucleotide encoding the variant provided in the present disclosure and operably linked to one or more regulatory sequences directing expression of a coding sequence in a suitable host cell under appropriate conditions.

The polynucleotide may be engineered in various manners allowing expression of the variant. Depending on the expression vector, it may be desirable or necessary to engineer the polynucleotide before inserting the polynucleotide into the vector. Such engineering may be performed using any method known in the art.

As used herein, the term "vector" refers to a DNA construct containing a base sequence of a polynucleotide encoding the variant and operably linked to a suitable expression regulatory region (expression regulatory sequence) so as to be able to express the variant of the present disclosure in a suitable host. The expression regulatory region may include a promoter capable of initiating transcription, any operator sequence for regulating the transcription, a sequence encoding a suitable mRNA ribosome binding site, and a sequence for regulating termination of transcription and translation. When a suitable host cell is transformed with the vector, the vector may replicate or function independently from the host genome or may integrate into the genome thereof.

The vector used in the present disclosure is not particularly limited and any vector known in the art may be used. Examples of common vectors include plasmids, cosmids, viruses, and bacteriophages in natural or recombinant states thereof. For example, as a phage vector or cosmid vector, pWE15, M13, MBL3, MBL4, IXII, ASHII, APII, t10, t11, Charon4A, and Charon21A may be used, and as a plasmid vector, pBR-based, pUC-based, pBluescriptll-based, pGEM-based, pTZ-based, pCL-based, and pET-based vectors may be used. Specifically, pDZ, pACYC177, pACYC184, pCL, pECCG117, pUC19, pBR322, pMW118, and pCC1BAC vectors may be used.

For example, the polynucleotide encoding the variant provided in the present disclosure may be inserted into the chromosome by using a vector for chromosomal insertion into cells. The insertion of the polynucleotide into the chromosome may be performed by any method known in the art, for example, homologous recombination, but is not limited thereto. The vector may further include a selection marker to detect chromosomal insertion. The selection marker is used to select cells that are transformed with the vector, that is, to confirm insertion of a target nucleic acid molecule, and markers providing selectable phenotypes, such as drug tolerance, nutrient requirement, resistance to cytotoxic agents, or expression of surface polypeptide may be used. Only cells expressing the selection marker are able to survive or to show different phenotypes under the environment treated with a selective agent, and thus the transformed cells may be selected.

The host cell of the present disclosure may include any host cell capable of expressing the variant of the present disclosure.

The host cell of the present disclosure may include the above-described variant, a polynucleotide encoding the variant, and a nucleic acid construct and/or vector including the same.

The nucleic acid construct or vector may be integrated into chromosome as described above or may be maintained as a self-replicating extrachromosomal vector.

The host cell of the present disclosure includes any progeny of a parent cell which is not identical to the parent cell due to mutation occurring during replication.

The host cell may be any cell useful for recombinant production of a variant, e.g., prokaryotic or eukaryotic cell.

The prokaryotic host cell may be any cell of gram-positive or gram-negative bacteria.

The gram-positive bacteria may include *Bacillus, Clostridium, Enterococcus, Geobacillus, Lactobacillus, Lactococcus, Oceanobacillus, Staphylococcus, Streptococcus,* and *Streptomyces*, but are not limited thereto.

The gram-negative bacteria may include *Campylobacter, Escherichia coli, Flavobacterium, Fusobacterium, Helicobacter, Iliobacter, Neisseria, Pseudomonas, Salmonella, Vibrio* (such as *Vibrio natriegens*), and *Ureaplasma*, but are not limited thereto.

In an embodiment, the bacterial host cell may be a host cell belonging to the genus *Escherichia*, specifically include *Escherichia coli* cell, but is not limited thereto.

In an embodiment, the bacterial host cell may be a host cell belonging to the genus *Bacillus*, specifically include *Bacillus alcalophilus, Bacillus amyloliquefaciens, Bacillus brevis, Bacillus circulans, Bacillus clausii, Bacillus coagulans, Bacillus furmus, Bacillus laatus, Bacillus lentus, Bacillus licheniformis, Bacillus megatelyum, Bacillus pumilus, Bacillus Stearothermophilus, Bacillus subtilis*, and *Bacillus thuringiensis* cells, without being limited thereto.

In an embodiment, the bacterial host cell may be a host cell belonging to the genus *Streptococcus*, specifically include *Streptococcus equisimilis, Streptococcus pyogenes, Streptococcus uberis,* and *Streptococcus equi* subsp. *Zooepidemicus* cells.

In an embodiment, the bacterial host cell may be a host cell belonging to the genus *Streptomyces*, specifically include *Streptomyces achromogenes, Streptomyces avermitilis, Streptomyces coelicola, Streptomyces griseus,* and *Streptomyces lividans* cell, without being limited thereto.

In an embodiment, the bacterial host cell may be a host cell belonging to the genus *Corynebacterium*, specifically include *Corynebacterium glutamicum, Corynebacterium crudilactis, Corynebacterium deserti, Corynebacterium efficiens, Corynebacterium callunae, Corynebacterium stationis, Corynebacterium singulare, Corynebacterium halotolerans, Corynebacterium striatum, Corynebacterium ammoniagenes, Corynebacterium pollutisoli, Corynebacterium imitans, Corynebacterium testudinoris,* or *Corynebacterium flavescens* cell, without being limited thereto.

The host cell may also be a eukaryotic cell, such as a mammalian, insect, plant, or fungal cell.

The host cell may be a fungal cell. In the present disclosure, the "fungi" includes not only the phyla Ascomycota, Basidiomycota, Chytridiomycota, and Zygomycota but also the Oomycota and all mitosporic fungi.

The fungal host cell may be a yeast cell. The "yeast" as used herein includes ascosporogenous yeast (Endomycetales), basidiosporogenous yeast, and yeast belonging to the Fungi Imperfecti (Blastomycetes). However, the classification of yeast may vary and yeast may be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Komagataella, Saccharomyces, Schizosaccharomyces,* or *Yarrowia* cell, such as *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Komagataella phaffii,* or *Yarrowia lipolytica* cell.

The fungal host cell may be a filamentous fungal cell. The "filamentous fungi" includes all filamentous forms of the subdivision Eumycota and Oomycota (as defined Hawksworth et al., 1995). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts, e.g., *Saccharomyces cerevisiae*, is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis*

*rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell. However, the present disclosure is not limited thereto.

A method for producing the variant of the present disclosure may include culturing a host cell.

As used herein, the term "culturing" refers to growing the host cell in an appropriately adjusted environment. A culturing process of the present disclosure may be performed according to an appropriate culture medium and culturing conditions well known in the art. The culturing process may be easily adjusted for use by those skilled in the art in accordance with a selected strain. Specifically, the culturing may be performed by a batch culture method, a continuous culture method, and a fed-batch culture method, without being limited thereto.

As used herein, the term "culture medium" refers to a mixture containing nutrients required for culturing the host cell as main ingredients and supplies nutrients and growth factors including water which are essential for survival and growth. Specifically, although the culture medium used to culture of the host cell and other culturing conditions according to the present disclosure are not particularly limited as long as the culture medium is commonly used for culturing host cells, the host cell of the present disclosure may be cultured in a common culture medium containing an appropriate carbon source, nitrogen source, phosphorus source, inorganic compound, amino acid and/or vitamin under aerobic conditions while adjusting temperature, pH, and the like.

In the present disclosure, the carbon source may include: carbohydrates such as glucose, sucrose, lactose, fructose, and maltose; sugar alcohols such as mannitol and sorbitol; organic acids such as pyruvic acid, lactic acid, and citric acid; and amino acids such as glutamic acid, methionine, and lysine. In addition, natural organic nutrients such as starch hydrolysates, molasses, blackstrap molasses, rice bran, cassava, sugar cane bagasse, and corn steep liquor may be used, and specifically carbohydrates such as glucose and sterile, pretreated molasses (i.e., molasses converted to reduced sugars) may be used, and suitable amounts of any other carbon sources may also be used without limitation. These carbon sources may be used alone or in combination of at least two thereof, but are not limited thereto.

As the nitrogen source, an inorganic nitrogen source such as ammonia, ammonium sulfate, ammonium chloride, ammonium acetate, ammonium phosphate, ammonium carbonate, and ammonium nitrate; and an organic nitrogen source such as amino acid, e.g., glutamic acid, methionine, and glutamine, peptone, NZ-amine, meat extract, yeast extract, malt extract, corn steep liquor, casein hydrolysate, fish or degradation products thereof, and defatted soybean cake or degradation products thereof may be used. These nitrogen sources may be used alone or in combination of at least two thereof, without being limited thereto.

As the phosphorus source, monopotassium phosphate, dipotassium phosphate, or sodium-containing salts corresponding thereto may be used. As an inorganic compounds, sodium chloride, calcium chloride, iron chloride, magnesium sulfate, iron sulfate, manganese sulfate, calcium carbonate, and the like may be used. The culture medium may further include amino acids, vitamins, and/or suitable precursors. These components or precursors may be added to the culture medium in a batch or continuous process. However, the present disclosure is not limited thereto.

In addition, while culturing the host cell of the present disclosure, compounds such as ammonium hydroxide, potassium hydroxide, ammonia, phosphoric acid, and sulfuric acid may be added to the culture medium in an appropriate manner to adjust the pH of the culture medium. In addition, a defoaming agent such as fatty acid polyglycol ester may be added during the culturing process to inhibit generation of foams. Also, oxygen or an oxygen-containing gas may be injected into the culture medium to maintain aerobic conditions of the culture medium or nitrogen, hydrogen, or carbon dioxide gas may be injected or no gas may be injected to maintain anaerobic and micro-aerobic conditions, without being limited thereto.

A temperature of the culture medium may be from 20° C. to 55° C., specifically from 25° C. to 40° C., but is not limited thereto. The culturing may be continued until a desired amount of a useful substance is obtained, specifically for 24 hours to 196 hours, without being limited thereto.

In an embodiment, the method for producing the modified polypeptide having mannanase activity of the present disclosure may further include recovering the modified polypeptide having mannanase activity of the present disclosure and expressed in the culturing step.

In another embodiment, the variant expressed in the culturing step may be recovered by using a method known in the art. For example, the variant may be recovered from a nutrient medium by any common procedure including, but is not limited to, collection, centrifugation, filtration, extraction, spray-drying, evaporation, or precipitation.

The recovering step may be performed by collecting the variant using an appropriate method known in the art according to the culturing method of the host cell of the present disclosure such as a batch, continuous, or fed-batch method. For example, centrifugation, filtration, treatment with a protein precipitating agent (salting out), extraction, ultrasonic disintegration, ultrafiltration, dialysis, various chromatographic methods such as molecular sieve chromatography (gel permeation), adsorption chromatography, ion exchange chromatography, and affinity chromatography, high-performance liquid chromatography (HPLC), any combination thereof may be used, and the variant may be recovered from the culture medium, or the host cell using an appropriate method known in the art.

In another embodiment, the variant expressed by the host cell in the culturing step may not be recovered. In a specified embodiment, the host cell expressing the variant may be used as a source of the variant.

A composition of the present disclosure may be used to decompose a mannan-containing substance.

The composition of the present disclosure may be used to convert the mannan-containing substance into mannose, mannobiose, mannotriose, or long-chain mannooligosaccharides.

The composition of the present disclosure may further include other components in addition to the variant provided in the present disclosure. Those skilled in the art may appropriately select components to be added to the composition of the present disclosure.

In an embodiment, the composition of the present disclosure may further include any component suitable for conversion of the mannan-containing substance into mannose, mannobiose, mannotriose, or long-chain mannooligosaccharides.

In an embodiment, the composition of the present disclosure may further include any component suitable for application to various industrial fields, such as animal feeds, baking, biomass saccharification, and pulp bleaching.

Examples of a substance added thereto include a stabilizer, a surfactant, a builder, a chelating agent, a dispersant, an enzyme, an enzyme stabilizer, a catalyst, an activator, a carrier, a mixture, a glidant, a disintegrant, an excipient, a solubilizer, a suspending agent, a pigment, a fragrance, a buffer, a preservative, an analgesic, an isotonic agent, a diluent, a lubricant, and the like, without being limited thereto.

In an embodiment, the composition provided in the present disclosure may further include a naturally occurring substance or a substance which does not occur naturally in addition to the variant provided in the present disclosure.

In an embodiment, the composition provided in the present disclosure may further include an additional enzyme commonly used in various industrial fields including animal feeds, baking, biomass saccharification, and pulp bleaching in addition to the variant provided in the present disclosure.

For example, the additional enzyme may further include at least one enzyme selected from the group consisting of β-amylase, cellulase (β-glucosidase, cellobiohydrolase, and endoglucanase), glucoamylase, hemicellulase (endo-mannanase, β-xylosidase, α-L-arabinofuranosidase, α-D-glucuronidase, feruloyl esterase, coumaroyl esterase, α-galactosidase, β-galactosidase, β-mannanase or β-mannosidase, isoamylase, isomerase, lipase, phytase, protease, pullulanase, and/or α-amylase and other commercially useful enzymes.

The mannanase variant of the present disclosure or the composition including the mannanase variant of the present disclosure may be used to decompose any mannan-containing substance.

In the present disclosure, the mannan-containing substance is any substance decomposed by mannanase. For example, the mannan-containing substance may be a substance selected from galactomannan, glucomannan, galactoglucomannan, locust bean gum, and mannan. For example, the mannan-containing substance may be mannan, without being limited thereto.

In a specific embodiment, the present disclosure provides a method for decomposing (or degrading) a mannan-containing substance. This may also be referred to as solubilization of mannan.

In an additional embodiment, the method is related to decomposition (e.g., degradation) of a polymer derived from decomposition of mannan.

The decomposition products (mannose, mannobiose, mannotriose, and long-chain mannooligosaccharides) may be used as energy sources of animals or feedstocks of fermentation processes, such as biofuels (e.g., bioethanol) and may also be used as prebiotics.

Mannan may be decomposed by using the variant of the present disclosure, the host cell expressing the same, and/or the composition including the variant and/or the host cell. In the hydrolysis step of mannan, a cofactor, a coenzyme, or the like may be added together with the variant of the present disclosure. A hydrolysis step of a substrate may be performed under optimal pH and temperature conditions which may be appropriately selected by those skilled in the art.

The mannanase variant of the present disclosure may be used in one of the following applications:
  a) as an additive in an animal feed ingredient; and/or
  b) as an animal feed supplement; and/or
  c) to decompose a grain-based substance (e.g., whole grains or parts of grains).

In an embodiment, the mannanase variant of the present disclosure may be used as a feed ingredient.

In an embodiment, the mannan-containing substance may be a feed ingredient or a feed component.

A feed composition of the present disclosure may refer to any natural or artificial diet, one meal, or components of the meal for animal to eat, ingest, and digest or suitable therefor, and may be prepared in various forms well known in the art.

In an embodiment, the mannanase variant of the present disclosure may be used in a food composition or preparation thereof.

In an embodiment, the mannan-containing substance may be a grain-based substance (whole grains, parts of grains, or malted grains, e.g., malted barley).

In an embodiment, the mannan-containing substance may be grain flour (e.g., wheat, oat, rye, or barley flour).

In an embodiment, the mannan-containing substance may be barley malt or mash, malted barley, or any combination thereof.

In an embodiment, the food composition may be a fermented drink including beer and wine. In another embodiment, the food composition may be a bakery product including robe, rolls, buns, pizzas, pretzels, tortillas, cakes, cookies, biscuits, and crackers. However, the present disclosure is not limited thereto.

The mannanase variant of the present disclosure may be used for wheat gluten-starch separation.

For example, after initial separation of wheat bran and wheat germ from wheat endosperm, fractionation of wheat endosperm flour into starch and gluten may be used to obtain high-quality α-starch and by-product β-starch, and active gluten.

In a method of separating grain flour (e.g., wheat flour) into starch and gluten, the method includes mixing the grain flour (e.g., wheat flour), water, and the mannanase variant. The grain flour, water, and mannanase variant may be mixed simultaneously or sequentially. In an embodiment, the grain flour (e.g., wheat flour) may be mixed with water before being mixed with the mannanase variant.

By applying the mannanase variant to wheat gluten-starch separation, a higher α-starch yield and/or gluten with higher quality (e.g., active gluten with higher quality) may be produced.

In another embodiment, the mannanase variant of the present disclosure may be used to decompose a grain-based substance and partially used in a process of producing a biofuel (e.g., bioethanol).

For example, the mannanase variant of the present disclosure may improve production of a biofuel (e.g., bioethanol) and use of a grain-based substance in the biofuel industry.

For example, a step of mixing the biofuel with the mannanase variant may be included before or during liquefaction, saccharification, fermentation, or simultaneous saccharification and fermentation, after fermentation, or in combination thereof.

When the mannanase variant of the present disclosure is applied to a biofuel production process, a saccharification solution containing more dry substances may be used; a higher solid content may be obtained in a final syrup; heat transfer may be improved; energy requirement may be lowered; contaminant adhered to an evaporator may decrease; cleaning costs may decrease: final fuel yields may increase: quality of by-products may be improved; solids and liquids may be more easily separated from residues after distillation; or a combination of these advantages may be obtained.

The mannanase variant of the present disclosure may be used in pulp bleaching.

For example, by treating pulp, in which colored lignin is connected to crystalline cellulose via xylan, with the mannanase variant, xylan may be decomposed and the colored lignin may be released, so that pulp bleaching may be promoted.

BRIEF DESCRIPTION OF DRAWINGS

FIG. 1 shows activity of the modified polypeptide of the present disclosure at a pH of 5.0 to pH 7.5.

FIG. 2 shows thermal tolerance of the modified polypeptide of the present disclosure.

MODE FOR CARRYING OUT THE INVENTION

Hereinafter, the present disclosure will be described in more detail with reference to the following examples. However, the following examples are merely for illustrating the present disclosure and are not intended to limit the scope of the present disclosure. Meanwhile, technical features not disclosed in the specification may be fully understood and implemented by those skilled in the art having ordinary knowledge in this technical field or relevant fields.

Example 1 Construction of Single Variant

Example 1-1 Construction of Random Variant

To cause random mutation in AnMAN, AnMAN variants substituted with various amino acids were constructed by gene amplification technology using manganese and Taq polymerase.

Specifically, a mutant gene library was prepared by PCR using the gene encoding *Aspergillus niger* mannanase (AnMAN) (SEQ ID NO: 2) as a template, primers, and a PCR premix (Taq 2× premix, Bioneer). The PCR was performed using Eppendorf Mastercycler Nexus GX2 and reaction conditions are as follows.

TABLE 1

| SEQ ID NO: | Name | Sequence (5'→3') |
|---|---|---|
| 9 | ORF(AnMAN)-F | TTCGTGATATACTGATAATAAATTGAATTTTCACACT |
| 10 | ORF(AnMAN)-R | AAACAGCCAAGCTTGCATGCCT |

TABLE 1-continued

| SEQ ID NO: | Name | Sequence (5'→3') |
|---|---|---|
| 11 | Vector-F | ATGCAAGCTTGGCTGTTTTGG |
| 12 | Vector-R | ATTATCAGTATATCACGAACAAAAAAGAG |

Initial denaturation: −95° C., 2 min
Denaturation: −95° C., 20 sec
Annealing: −50° C., 10 sec
Extension: −72° C., 1 min (30 cycles from denaturation to extension)
Final Extension: −72° C., 5 min The amplified mutant gene was cloned to a pHCE vector having HCE promoter by using In-Fusion HD cloning kit (Takara, Cat. No. 639650). Then, *E. coli* BL21 strain was transformed with the vector, and colonies were inoculated intoan LB medium of a 96-deep-well plate (Bioneer) and cultured to evaluate properties. The culture medium was mixed with BugBuster (Merck) at 1:1 and the cells were disrupted. A crude enzyme solution (lysate) was isolated by centrifugation and seeded on a new 96 well plate (SPL) in an appropriate amount, and then mixed with a 0.3% mannan solution at 1:1, followed by enzymatic reaction using a phosphate buffer at pH 7.0. After 10 minutes, the reaction was terminated by adding a suitable amount of the DNS solution and the resultant was maintained in an oven at 85° C. for 20 minutes for color development. Then, activity was measured at an absorbance of 540 nm. Variants having enhanced activity were selected and positions of modification were identified.

A method for preparing a DNS solution of the present disclosure is as follows. 6.3 g of 3,5-dinitrosalicylic acid (samchun, D1267), accurately weighed, and 21 g of sodium hydroxide (Daejung, 7571-4400) were added to a beaker containing 500 mL of distilled water at 50° C. 5 g of phenol (Sigma-Aldrich, P1037) and 5 g of sodium sulfite anhydrous (Daejung, 7634-4405) were added to a pre-solution prepared by dissolving 182 g of potassium sodium tartrate tetrahydrate (Daejung, 6618-4400) in 300 ml of water while heating, and stirred. They were mixed while stirring until the components are completely dissolved, and then cooled and filtered using 1000 mL of distilled water.

As a result, proteins having amino acid sequences of SEQ ID NOS: 3 to 5 were confirmed.

Example 1-2 Purification of Single Variant

*E. coli* BL21 strains respectively transformed with single variants (respectively, SEQ ID NOS: 3 to 5) prepared in Example 1-1 above and exhibiting excellent activity and a gene encoding AnMAN were inoculated into 5 mL of a sterile LB kanamycin medium (BD Difco) and cultured at 37° C. at 200 rpm for 12 hours. The cultured strains were transferred to 400 mL of an LB kanamycin medium and a main culture was performed at 37° C. at 200 rpm for 24 hours, and then strains were recovered by centrifugation. The recovered strains were re-dispersed by adding 20 ml of a lysis buffer (50 mM Tris-HCl PH 8.0, 100 mM NaCl, 10 mM imidazole) thereto, followed by sonication and centrifugation to obtain a lysate. After adsorbing the lysate onto a Ni-NTA resin (Qiagen, Cat No. 30230) by flowing the lysate, a washing buffer (in which only the concentration of imidazole contained in the lysis buffer was modified to 20 mM), an elution buffer (in which only the concentration of imidazole contained in the lysis buffer was modified to 250 mM) were sequentially flowed thereto to obtain purified single variants and purified AnMAN.

Example 2 Construction of Combined Variant

Example 2-1 Construction of Combined Variant

Among the single variants prepared in Example 1-1 above and exhibiting excellent activity, a variant including a combination of mutation positions of SEQ ID NOS: 3 and 4 was constructed. Specifically, the variant was constructed by PCR using the template (SEQ ID NO: 2), primers, and a PCR premix (Taq 2× premix, Bioneer). The PCR was performed using Eppendorf Mastercycler Nexus GX2 and reaction conditions are as follows.

TABLE 2

| SEQ ID NO: | Name | Sequence (5'→3') |
|---|---|---|
| 13 | SEQ ID NO: 3-N | GCGGGTACAAATACCTACTGGATCGGA |
| 14 | SEQ ID NO: 3-R | TCCGATCCAGTAGGTATTTGTACCCGC |
| 15 | SEQ ID NO: 4-N | GGTGGATCTGGTGTGACAGACTTTTAC |
| 16 | SEQ ID NO: 4-R | GTAAAAGTCTGTCACACCAGATCCACC |

Initial denaturation: ~95° C., 2 min
Denaturation: ~95° C., 20 sec
Annealing: ~50° C., 10 sec
Extension: ~72° C., 1 min (30 cycles from denaturation to extension)
Final Extension: ~72° C., 5 min The amplified gene was cloned to a pHCE vector having a constitutive expression system by using an In-Fusion HD cloning kit (Takara, Cat. No. 639650). Then, *E. coli* Dh5α was transformed with the vector and a protein having an amino acid sequence of SEQ ID NO: 6 was confirmed by sequencing.

Example 2-2 Purification of Combined Variant

*E. coli* BL21 strains transformed with a gene encoding the combined variant (SEQ ID NO: 6) prepared in Example 2-1 above were inoculated into 5 mL of an LB kanamycin medium (BD Difco) and cultured at 37° C. at 200 rpm for 12 hours. The cultured strains were transferred to 400 mL of an LB kanamycin medium and a main culture was performed at 37° C. at 200 rpm for 24 hours, and then strains were recovered by centrifugation. The recovered strains were re-dispersed by adding 20 ml of a lysis buffer (50 mM Tris-HCl pH 8.0, 100 mM NaCl, 10 mM imidazole) thereto, followed by sonication and centrifugation to obtain a lysate. After adsorbing the lysate onto a Ni-NTA resin (Qiagen, Cat. No. 30230) by flowing the lysate, a washing buffer (in which only the concentration of imidazole contained in the lysis buffer was modified to 20 mM), an elution buffer (in which only the concentration of imidazole contained in the lysis buffer was modified to 250 mM) were sequentially flowed thereto to obtain purified combined variant.

Experimental Example 1 Confirmation of Activity of Mannanase Variant at Different pH Levels In order to measure activity of the mannanase variants at different PH levels, an appropriate amount of each of the purified variants and the purified AnMAN prepared in Examples 1-2 and 2-2 was mixed with a 0.3% mannan solution, followed by enzymatic reaction in an acetic acid buffer at pH 5.5 and in a phosphate buffer at pH 7.0. Then, after performing the reaction at 37° C. for 10 minutes, an appropriate amount of the DNS solution was added to stop the reaction. Subsequently, the solution was maintained at 100° C. for 10 minutes for color development, and activity was measured and evaluated at an absorbance of 540 nm.

Enzymatic activity was calculated as relative activity (%) and listed in FIG. 1 and Table 3 below.

Specifically, the wild-type indicates activity of the enzyme using the *E. coli* BL21 strain transformed with the gene encoding AnMAN (SEQ ID NO: 2) and SEQ ID NOS: 3 to 6 indicate activity of the enzyme using the *E. coli* BL21 strains respectively transformed with the genes encoding the variants of SEQ ID NOS: 3 to 6.

TABLE 3

| Reaction Conditions | Wild-type | SEQ ID NO: 3 | SEQ ID NO: 4 | SEQ ID NO: 5 | SEQ ID NO: 6 |
|---|---|---|---|---|---|
| pH 5.5 | 100 | 135 | 145 | 135 | 158 |
| pH 7.0 | 100 | 150 | 160 | 149 | 177 |

As a result, as shown in FIG. 1 and Table 3 above, it was confirmed that the three types of single variants (SEQ ID NOS: 3, 4, and 5) had higher activity by 50%, 60%, and 49%) and the one type of combined variant (SEQ ID NO: 6) had higher activity by 77%, compared to the AnMAN (wild-type) exhibiting relatively low activity, under the pH conditions of 5.5 to 7.0.

Experimental Example 2 Confirmation of Thermal Tolerance of Combined Variant of Mannanase In order to identify thermal tolerance of the mannanase variants, thermal tolerance was evaluated using the purified variants and the purified AnMAN prepared in Examples 1-2 and 2-2 by using the *E. coli* BL21 strains respectively transformed with the gene encoding AnMAN (SEQ ID NO: 2) and the gene encoding the combined variant (SEQ ID NO: 6).

Specifically, after maintaining the purified variants and the purified AnMAN at 40° C., 50° C., 60° C., 70° C., and 80° C. for 5 minutes each, they were mixed with a 0.3% mannan solution and an acetic acid buffer solution with a pH of 5.5, followed by reaction at 37° C. for 10 minutes. After the reaction, the reaction was terminated by adding an appropriate amount of the DNS solution thereto. Then, the mixed solution was maintained at 100° C. for 10 minutes for color development, and thermal tolerance was evaluated at an absorbance of 540 nm.

As a result, as shown in FIG. 2, it was confirmed that the combined variant (SEQ ID NO: 6) had similar thermal tolerance to that of the AnMAN (wild-type).

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. Therefore, the scope of the disclosure is defined not by the detailed description, but by the claims and their equivalents, and all variations within the scope of the claims and their equivalents are to be construed as being included in the disclosure.

The invention claimed is:

1. A modified polypeptide having mannanase activity and consisting of an amino acid sequence as set forth in one of SEQ ID NOS: 3 to 6.

2. The modified polypeptide according to claim 1, wherein the modified polypeptide has enhanced enzymatic activity in a pH range of 5.0 to 9.0 compared to a polypeptide consisting of an amino acid sequence of SEQ ID NO: 1.

3. The modified polypeptide according to claim 1, wherein the modified polypeptide has enhanced thermal tolerance and/or thermal stability compared to a polypeptide consisting of an amino acid sequence of SEQ ID NO: 1.

4. A composition comprising the modified polypeptide according to claim 1.

5. A composition for reaction with a mannan-containing substance, the composition comprising the modified polypeptide according to claim 1.

6. A method for producing mannose, mannobiose, mannotriose, or long-chain mannooligosaccharides, the method comprising bringing a mannan-containing substance into contact with the modified polypeptide according to claim 1, a host cell expressing the modified polypeptide, and/or a composition comprising the modified polypeptide.

7. A method for decomposing a mannan-containing substance, the method comprising treating a substrate with the modified polypeptide according to claim 1, a host cell expressing the modified polypeptide, and/or a composition comprising the modified polypeptide.

8. A polynucleotide encoding the modified polypeptide according to claim 1.

9. A nucleic acid construct comprising the polynucleotide according to claim 8.

10. A vector comprising the polynucleotide according to claim 8 or the nucleic acid construct according to claim 9.

11. A host cell comprising the modified polypeptide according to claim 1.

12. A method for preparing a modified polypeptide having mannanase activity, the method comprising culturing the host cell according to claim 11.

13. The method according to claim 12, further comprising recovering the modified polypeptide having mannanase activity according to claim 1 and expressed in the culturing step.

* * * * *

SEQUENCE LISTING

```
Sequence total quantity: 16
SEQ ID NO: 1            moltype = AA   length = 345
FEATURE                 Location/Qualifiers
REGION                  1..345
                        note = Mannanase
source                  1..345
                        mol_type = protein
                        organism = synthetic construct
SEQUENCE: 1
SFASTSGLQF TIDGETGYFA GTNSYWIGFL TDNADVDLVM GHLKSSGLKI LRVWGFNDVT   60
SQPSSGTVWY QLHQDGKSTI NTGADGLQRL DYVVSSAEQH DIKLIINFVN YWTDYGGMSA  120
YVSAYGGSGE TDFYTSDTMQ SAYQTYIKTV VERYSNSSAV FAWELANEPR CPSCDTSVLY  180
NWIEKTSKFI KGLDADRMVC IGDEGFGLNI DSDGSYPYQF SEGLNFTMNL GIDTIDFGTL  240
HLYPDSWGTS DDWGNGWITA HGAACKAAGK PCLLEEYGVT SNHCSVEGSW QKTALSTTGV  300
GADLFWQYGD DLSTGKSPDD GNTIYYGTSD YQCLVTDHVA AIGSA               345

SEQ ID NO: 2            moltype = DNA  length = 1035
FEATURE                 Location/Qualifiers
misc_feature            1..1035
                        note = Mannanase
source                  1..1035
                        mol_type = other DNA
                        organism = synthetic construct
SEQUENCE: 2
agttttgctt ctacatcagg actacaattc accatcgatg gtgagacagg ttatttcgcc    60
ggtacaaata gttactggat cggttttctg accgacaacg cagatgtgga tcttgttatg   120
ggtcatctga aaagcagcgg cttgaagatc ctgcgtgtat ggggtttcaa cgacgttacc   180
tctcagccga gcagcgggac ggtctggtat caactgcacc aagatggaaa aagcaccatt   240
aacaccggtg cggatggcct ccagcgtctg gattacgtcg tgagcagcgc tgaacagcac   300
gatatcaaac tgattattaa cttcgtgaac tattggaccg actacggcgg tatgagcgcg   360
tacgtgagcg cgtacggcgg ctctggcgaa accgatttct acacctcgga taccatgcag   420
agcgcgtacc aaacctatat caaaaccgtg gtggagcgct atagcaacag cagcgctgtg   480
tttgcttggg aactggcaaa tgaaccgcgt tgcccgtctt gtgatacctc cgtgctgtac   540
aactggatcg agaaaacctc caaattcatc aagggtttag acgccgaccg catggtttgc   600
attggcgatg aggttcgg cctgaacatc gacagcgatg gcagctaccc gtatcagttc   660
agcgaaggcc tgaattttac catgaatctg ggtattgaca ccatcgattt tggtacgttg   720
catctgtacc cagattcctg gggtacgtcc gacgactggg gcaacggttg gattaccgca   780
catggtgctg cgtgtaaagc agccggtaag ccgtgcctgc tggaagagta tggtgttacc   840
agcaatcatt gcagcgttga gggcagttgg caaaaaactg cgctgagcac gaccggtgtt   900
ggtgcggatc tgttttggca gtatggcgat gacctctcaa cgggcaaatc cccggatgat   960
ggcaacacta tttattacgg cacctctgac taccaatgtc tggttactga ccacgtcgcg  1020
gcgattggtt ctgcg                                                   1035

SEQ ID NO: 3            moltype = AA   length = 345
FEATURE                 Location/Qualifiers
REGION                  1..345
                        note = Mannanase variant
source                  1..345
                        mol_type = protein
                        organism = synthetic construct
SEQUENCE: 3
SFASTSGLQF TIDGETGYFA GTNTYWIGFL TDNADVDLVM GHLKSSGLKI LRVWGFNDVT   60
SQPSSGTVWY QLHQDGKSTI NTGADGLQRL DYVVSSAEQH DIKLIINFVN YWTDYGGMSA  120
YVSAYGGSGE TDFYTSDTMQ SAYQTYIKTV VERYSNSSAV FAWELANEPR CPSCDTSVLY  180
NWIEKTSKFI KGLDADRMVC IGDEGFGLNI DSDGSYPYQF SEGLNFTMNL GIDTIDFGTL  240
HLYPDSWGTS DDWGNGWITA HGAACKAAGK PCLLEEYGVT SNHCSVEGSW QKTALSTTGV  300
GADLFWQYGD DLSTGKSPDD GNTIYYGTSD YQCLVTDHVA AIGSA               345

SEQ ID NO: 4            moltype = AA   length = 345
FEATURE                 Location/Qualifiers
REGION                  1..345
                        note = Mannanase variant
source                  1..345
                        mol_type = protein
                        organism = synthetic construct
SEQUENCE: 4
SFASTSGLQF TIDGETGYFA GTNSYWIGFL TDNADVDLVM GHLKSSGLKI LRVWGFNDVT   60
SQPSSGTVWY QLHQDGKSTI NTGADGLQRL DYVVSSAEQH DIKLIINFVN YWTDYGGMSA  120
YVSAYGGSGV TDFYTSDTMQ SAYQTYIKTV VERYSNSSAV FAWELANEPR CPSCDTSVLY  180
NWIEKTSKFI KGLDADRMVC IGDEGFGLNI DSDGSYPYQF SEGLNFTMNL GIDTIDFGTL  240
HLYPDSWGTS DDWGNGWITA HGAACKAAGK PCLLEEYGVT SNHCSVEGSW QKTALSTTGV  300
GADLFWQYGD DLSTGKSPDD GNTIYYGTSD YQCLVTDHVA AIGSA               345
```

```
SEQ ID NO: 5                moltype = AA   length = 345
FEATURE                     Location/Qualifiers
REGION                      1..345
                            note = Mannanase variant
source                      1..345
                            mol_type = protein
                            organism = synthetic construct
SEQUENCE: 5
SFASTSGLQF TIDGETGYFA GTNSYWIGFL TDNADVDLVM GHLKSSGLKI LRVWGFNDVT    60
SQPSSGTVWY QLHQDGKSTI NTGADGLQRL DYVVSSAEQH DIKLIINFVN YWTDYGGMSA   120
YVSAYGGSGE TDFYTSDTMQ SAYQTYIKTV VERYSNSSAV FAWELANEPR CPSCDTSVLY   180
NWIEKTSKFI KGLDADRMVC IGDEGFGLNI DSDGSYPYQF SEGLNFTMNL GIDTIDFGTL   240
HLYPDSWGTS DDWGNGWITA HCAACKAAGK PCLLEEYGVT SNHCSVEGSW QKTALSTTGV   300
GADLFWQYGD DLSTGKSPDD GNTIYYGTSD YQCLVTDHVA AIGSA                  345

SEQ ID NO: 6                moltype = AA   length = 345
FEATURE                     Location/Qualifiers
REGION                      1..345
                            note = Mannanase variant
source                      1..345
                            mol_type = protein
                            organism = synthetic construct
SEQUENCE: 6
SFASTSGLQF TIDGETGYFA GTNTYWIGFL TDNADVDLVM GHLKSSGLKI LRVWGFNDVT    60
SQPSSGTVWY QLHQDGKSTI NTGADGLQRL DYVVSSAEQH DIKLIINFVN YWTDYGGMSA   120
YVSAYGGSGV TDFYTSDTMQ SAYQTYIKTV VERYSNSSAV FAWELANEPR CPSCDTSVLY   180
NWIEKTSKFI KGLDADRMVC IGDEGFGLNI DSDGSYPYQF SEGLNFTMNL GIDTIDFGTL   240
HLYPDSWGTS DDWGNGWITA HGAACKAAGK PCLLEEYGVT SNHCSVEGSW QKTALSTTGV   300
GADLFWQYGD DLSTGKSPDD GNTIYYGTSD YQCLVTDHVA AIGSA                  345

SEQ ID NO: 7                moltype = AA   length = 383
FEATURE                     Location/Qualifiers
REGION                      1..383
                            note = Mannanase
source                      1..383
                            mol_type = protein
                            organism = synthetic construct
SEQUENCE: 7
MKLSNALLTL ASLALANVST ALPKASPAPS TSSSAASTSF ASTSGLQFTI DGETGYFAGT    60
NSYWIGFLTD NADVDLVMGH LKSSGLKILR VWGFNDVTSQ PSSGTVWYQL HQDGKSTINT   120
GADGLQRLDY VVSSAEQHDI KLIINFVNYW TDYGGMSAYV SAYGGSGETD FYTSDTMQSA   180
YQTYIKTVVE RYSNSSAVFA WELANEPRCP SCDTSVLYNW IEKTSKFIKG LDADRMVCIG   240
DEGFGLNIDS DGSYPYQFSE GLNFTMNLGI DTIDFGTLHL YPDSWGTSDD WGNGWITAHG   300
AACKAAGKPC LLEEYGVTSN HCSVEGSWQK TALSTTGVGA DLFWQYGDDL STGKSPDDGN   360
TIYYGTSDYQ CLVTDHVAAI GSA                                          383

SEQ ID NO: 8                moltype = DNA   length = 1149
FEATURE                     Location/Qualifiers
misc_feature                1..1149
                            note = Mannanase
source                      1..1149
                            mol_type = other DNA
                            organism = synthetic construct
SEQUENCE: 8
atgaagcttt ccaacgccct cctcaccctg gctagcctgg cgctggccaa cgtctccacg    60
gctctgccga aagcctcccc tgcaccgagc accagcagca gtgctgcctc caccagcttc   120
gccagcactt ctgggcttca atttaccatc gacggtgaga caggctactt cgcgggtaca   180
aattcttact ggatcggatt cttgaccgat aatgccgacg ttgaccttgt gatgggtcat   240
cttaagagta gtgggttaaa aattcttaga gtctgggggt tcaatgatgt gacttcgcag   300
ccctccagcg gaaccgtgtg gtaccaactt catcaggatg gaaagtccac tattaacacg   360
ggcgcggatg gcttgcagcg cctggactac gttgtatcga gcgccgagca acacgatatc   420
aaacttatca taaacttcgt aaattattgg acagattacg gtggaatgtc agcgtacgtt   480
agcgcttacg gtggatctgg tgaaacagac ttttacactt cagacacgat gcagtcagcc   540
tatcagacct atattaagac cgtagtggaa cgctacttcag cagtgtttcg   600
tgggaattgg caaatgagcc acgttgcccc tcttgcgata ctagtgttct ttacaactgg   660
attgaaaaga catcaaaatt catcaaaggt ctggacgcag acagaatggt ttgtatcgga   720
gatgagggct tcgattaaa catcgactct gacgggtcat atccatatca attctccgaa   780
gggtttaaatt ttactatgaa cttagggata gacactattg atttcggtac gctgcacttg   840
taccctgact cctgggcac ctcggatgat tggggaaatg gctggataac ggctcatgtt   900
gcggcatgca aggccgctgg aaaaccatgt ttattagagg agtacggcgt cacaagcaat   960
cattgcagcg tggaaggtag ttggcaaaag acagcactgt caaccacagg ggtcggcgcg  1020
gacctgtttt ggcagtacgg ggatgactta agcacaggaa agtcccccga tgatggaaat  1080
acaatatact acggtacatc tgattaccag tgcctggtta ctgaccatgt cgccgccatc  1140
ggctctgca                                                         1149

SEQ ID NO: 9                moltype = DNA   length = 37
FEATURE                     Location/Qualifiers
misc_feature                1..37
                            note = ORF(AnMAN)-F
```

```
source                  1..37
                        mol_type = other DNA
                        organism = synthetic construct
SEQUENCE: 9
ttcgtgatat actgataata aattgaattt tcacact                                    37

SEQ ID NO: 10           moltype = DNA   length = 22
FEATURE                 Location/Qualifiers
misc_feature            1..22
                        note = ORF(AnMAN)-R
source                  1..22
                        mol_type = other DNA
                        organism = synthetic construct
SEQUENCE: 10
aaacagccaa gcttgcatgc ct                                                    22

SEQ ID NO: 11           moltype = DNA   length = 21
FEATURE                 Location/Qualifiers
misc_feature            1..21
                        note = Vector-F
source                  1..21
                        mol_type = other DNA
                        organism = synthetic construct
SEQUENCE: 11
atgcaagctt ggctgttttg g                                                     21

SEQ ID NO: 12           moltype = DNA   length = 29
FEATURE                 Location/Qualifiers
misc_feature            1..29
                        note = Vector-R
source                  1..29
                        mol_type = other DNA
                        organism = synthetic construct
SEQUENCE: 12
attatcagta tatcacgaac aaaaaagag                                             29

SEQ ID NO: 13           moltype = DNA   length = 27
FEATURE                 Location/Qualifiers
misc_feature            1..27
                        note = SEQ ID NO: 3-N
source                  1..27
                        mol_type = other DNA
                        organism = synthetic construct
SEQUENCE: 13
gcgggtacaa atacctactg gatcgga                                               27

SEQ ID NO: 14           moltype = DNA   length = 27
FEATURE                 Location/Qualifiers
misc_feature            1..27
                        note = SEQ ID NO: 3-R
source                  1..27
                        mol_type = other DNA
                        organism = synthetic construct
SEQUENCE: 14
tccgatccag taggtatttg tacccgc                                               27

SEQ ID NO: 15           moltype = DNA   length = 27
FEATURE                 Location/Qualifiers
misc_feature            1..27
                        note = SEQ ID NO: 4-N
source                  1..27
                        mol_type = other DNA
                        organism = synthetic construct
SEQUENCE: 15
ggtggatctg gtgtgacaga cttttac                                               27

SEQ ID NO: 16           moltype = DNA   length = 27
FEATURE                 Location/Qualifiers
misc_feature            1..27
                        note = SEQ ID NO: 4-R
source                  1..27
                        mol_type = other DNA
                        organism = synthetic construct
SEQUENCE: 16
gtaaaagtct gtcacaccag atccacc                                               27
```